United States Patent [19]

Sugano et al.

[11] Patent Number: 4,738,931

[45] Date of Patent: Apr. 19, 1988

[54] HUMAN INTERFERON-β GENE

[75] Inventors: Haruo Sugano; Tadatsugu Taniguchi; Shigeo Ono, all of Tokyo, Japan

[73] Assignee: Juridical Foundation, Japanese Foundation for Cancer Research, Tokyo, Japan

[21] Appl. No.: 70,120

[22] Filed: Jul. 6, 1987

Related U.S. Application Data

[63] Continuation of Ser. No. 718,181, Mar. 29, 1985, abandoned, which is a continuation of Ser. No. 432,934, Sep. 30, 1982, abandoned.

[30] Foreign Application Priority Data

Feb. 4, 1981 [JP] Japan ................................. 56-14373
Jul. 11, 1981 [JP] Japan ................................ 56-108539

[51] Int. Cl.$^4$ ..................... C12N 1/00; C12N 15/00; C12N 1/20; C12N 5/00; C12P 21/02; C12P 21/04; C12P 19/34; C07H 21/04
[52] U.S. Cl. .................................. 435/320; 435/70; 435/71; 435/91; 435/172.1; 435/172.3; 435/253; 435/811; 435/240.2; 536/27; 935/11; 935/29; 935/34; 935/36; 935/41
[58] Field of Search .................. 435/68, 70, 71, 91, 435/172.1, 173, 243, 253, 317.1, 320, 811; 536/27; 935/11, 29, 34, 36, 41

[56] References Cited

PUBLICATIONS

Taniguchi et al: Proc. Natl. Acad. Sci. USA 77, 5230 (1980).
Maniatis et al: Cell 15, 687 (1978).
Houghton: Nature 285, 536 (1980).
Helling et al: in *Genetic Engineering*, Chakrabarty (ed.), CRC Press, 1978, p. 8.
Gross et al: Nucl. Acids Res. 9, 2495 (1981).
Degrave et al: Gene 14, 137 (1981).
Houghton et al: Nucl. Acids Res. 9, 247 (1981).
Derynck et al: Nature 283, 542 (1980).
Mory et al, "Synthesis of Human Interferon Beta-1 in *Escherichia coli* Infected by a Lambda Phage Recombinant Containing a Human Genomic Fragment", Chem. Abstr. 95: 165477k (1981) of Eur. J. Biochem. 120: 197 (1981).
Corden et al, "Promoter Sequences of Eukaryotic Protein-Coding Genes", Science 209: 1406 (1980).
Ohno et al., Proc. Natl. Acad. Sci., U.S.A., vol. 78, No. 9 (Sep. 1981) 5305–5309.
Lawn et al., Nuc. Acids Res., vol. 9, No. 5 (1981) 1045–1052.
Houghton et al., Nuc. Acids Res., vol. 9, No. 2 (1981) 247–266.
Ohno et al., Nuc. Acids Res., vol. 10, No. 3 (1982) 967–977.
Mory et al., Eur. J. Bioch., vol. 120 (1981) 197–202.
T. Taniguchi, et al., Gene, 10, 11–15 (1980).
Thomas C. Currier, et al., Analytical Biochemistry 76, 431–441 (1976).
Dennis R. Roop, et al., Cell 15, 671–688 (1978).
W. David Benton, et al., Science 196, 180–182 (1977).
E. M. Southern, Journal of Molecular Biology 98, 503–517 (1975).
Hamilton O. Smith, et al., Nucleic Acids Research 3, 2387–2398 (1976).
Maxamo et al., Proceedings of the National Academy of Sciences U.S.A. 74, 560–564 (1977).
Michael Grunstein, et al., Proceedings of the National Academy of Sciences U.S.A. 72, 3961–3965 (1975).
Vicenzo Pirrotta, Nucleic Acids Research 3, 1747 (1976).

(List continued on next page.)

*Primary Examiner*—James Martinell
*Attorney, Agent, or Firm*—Fitzpatrick, Cella, Harper & Scinto

[57] ABSTRACT

The present invention relates to human interferon-β gene derived from human chromosome, a DNA containing said gene and a DNA responsible for control of its transcription and a recombinant DNA of said DNA and a vector DNA. The gene and DNA of the present invention are introduced in eukaryotic cells and used for the production of human interferon-β.

2 Claims, 1 Drawing Sheet

PUBLICATIONS

Robert Old, et al., Journal of Molecular Biology 92, 331 (1975).

Gary A. Wilson, et al., Journal of Molecular Biology 97, 123 (1975).

David I. Smith, et al., Nucleic Acids Research 3, 343 (1976).

Richard J. Roberts, Gene 8, 329-343 (1980).

Kiranur N. Subramanian, et al., Journal of Molecular Biology 110, 297 (1977).

Richard J. Roberts, et al., Journal of Molecular Biology 102, 157 (1976).

H. F. Tabak, et al., Nucleic Acids Research 5, 2321-2332 (1978).

Frederick R. Blattner, et al., Science 202, 1279-1284 (1978).

Tom Maniatis, et al., Cell 15, 687-701 (1978).

Vincenzo Enea, et al, Journal of Molecular Biology 96, 495-509 (1975).

Middleton, et al, Journal of Virology, 10, No. 1, 42 (1972).

FIG. 1

HUMAN INTERFERON-β GENE

This application is a continuation of application Ser. No. 718,181, filed Mar. 29, 1985, now abandoned, which is a continuation of application Ser. No. 432,934, filed Sept. 30, 1982, also now abandoned.

TECHNICAL FIELD

The present invention relates to human interferon-β gene derived from human chromosome [DNA (deoxyribonucleic acid) corresponding to entire region coding for interferon-β gene], a DNA containing said gene and a DNA responsible for control of transcription of said gene and a recombinant DNA of said DNA and a vector DNA.

BACKGROUND ART

It has been known that a cDNA of human interferon-β is prepared using mRNA as a template. [Gene, 10, 11–15, (1980)].

DISCLOSURE OF THE INVENTION

The present inventors have studied about the mass production of interferon using a recombinant DNA wherein human interferon gene is inserted into a plasmid DNA, for example, a plasmid DNA derived from *Escherichia coli* or a phage DNA, for example, λphage DNA derived from *Escherichia coli* by recombinant DNA technology.

As a result, it has been found that human interferon-β can be produced by propagating and multiplying a novel recombinant in bacteria such as *Escherichia coli* and a compound having the same structure as human interferon-β can also be produced by inserting the recombinant into a chromosomal gene of eukaryotic cells such as mouse cells or a virus and incorporating the resultant recombinant into eukaryotic cells. Thus the present invention has been completed.

The recombinant DNA is a novel one having at least an entire region coding for human interferon-β gene in chromosome and furthermore containing a region which is believed to be responsible for the control of transcription.

In the present invention, human interferon-β gene and a DNA containing the same and a DNA responsible for control of its transcription are recovered directly from human chromosomal gene.

The present invention is explained in detail below.

The present invention relates to a human interferon-β gene derived from human chromosome, a DNA containing said gene and a DNA responsible for control of its transcription and a recombinant DNA of the DNA and a vector DNA.

The recombinant DNA of the present invention is prepared by the following procedure.

An entire DNA of human chromosome such as chromosomal DNA extracted from human fetal liver is cut with a restriction endonuclease in a proper length.

All fragments or selected fragments with proper length are concentrated by electrophoresis, etc. The fragments are inserted into a vector DNA by recombinant DNA technology to obtain recombinant DNAs. The novel recombinant DNA having human inteferon-β gene in chromosome is selected and isolated from the recombinant DNAs using as a probe the recombinant DNA containing a DNA showing complementarity to the human interferon-β messenger RNA, i.e. human inteferon-β cDNA, and being labelled with a radio isotope.

The process for producing said recombinant DNA is specifically explained more in detail.

Human chromosomal DNAs are extracted from human fetal liver with phenol, etc. The extracted DNAs are subjected to partial digestion with restriction endonucleases such as HaeIII, AluI, etc, to cut appropriately.

The thus obtained entire DNA fragments of human chromosome are joined with EcoRI linker, etc. and inserted into a DNA such as phageλ of *Escherichia coli*, using bacteriophage T4 ligase to obtain recombinant DNAs.

The recombinant DNAs are modified to more infectious λphages by packaging method. The thus obtained whole recombinant DNAs containing entire human genes are called human gene library.

The human gene library contains almost all human gene DNAs as apparent from the construction method and most of the human genes can be isolated therefrom.

Since cleavage map for restriction endonucleases around human interferon-β gene in chromosome has been determined as mentioned below, the human whole gene library as a starting human interferon-β gene may be replaced with the following more concentrated recombinant.

That is, the entire human chromosomal DNA is digested completely with restriction endonuclease HindIII, etc. and subjected to agarose gel electrophoresis to obtain DNA fragments of about 10 kilobase (hereinafter referred to as Kb).

A DNA library having a length of about 10 Kb and HindIII cleavage sites at both ends is obtained by inserting the obtained fragments into λphage described above. Human interferon-β gene in chromosome is included in the DNA of about 10 Kb in the DNA library which seems to be concentrated about 10-fold over the whole gene library.

As the vector, Charon phages, plasmids such as pBR322, pCR1, pMB9, pSC1, and the like may be used instead of λphage.

A recombinant DNA having DNA fragment containing human interferon-β gene may be selected from the thus obtained human gene library as follows.

A recombinant plasmid having a structure (cDNA) which is complementary to human inteferon-β messenger RNA is isolated from *Escherichia coli* χ1776/TpIF319-13 ATCC 31712 according to the method of Currier and Nester [Analyt. Biochem. Vol. 76, 431–441 (1976)]. The plasmid labelled with [$^{32}$P] according to nick translation method [Roop et al. Cell 15, 671–685 (1978)] is used as a probe.

The gene library prepared using *Escherichia coli* phage as a vector as mentioned above is dispersed on an agar plate and DNAs in phage plaques corresponding to each clone are fixed on a filter according to the method of Bentonn and Davis [Science, 196, 180–182 (1977)].

The filter is subjected to hybridization using the probe mentioned above and a cloned phage having a DNA hybridizing with the recombinant having a structure complementary to human interferon-β messenger RNA is isolated by radioautography.

The thus obtained phage is propagated and a DNA is extracted therefrom. The DNA is treated with restriction endonuclease such as EcoRI and the mixture is fractionated by agarose gel electrophoresis. The obtained fractions are fixed on a filter according to Southern method [J. Mol. Biol. 98, 503–517 (1975)]. Hybridization is carried out using the probe described above, for so called Southern blotting analysis (the same reference as mentioned above).

Thus, a phage clone having EcoRI fragment of 1.8 Kb which hybridizes with the cDNA is obtained.

More detailed restriction endonuclease map is prepared by the method of Smith and Birnstiel [Nucleic Acids Res. 3, 2387–2398 (1976)].

Further, DNA base sequence is determined according to, for example, the method of Maxam and Gilbert [Proc. Natl. Acad. Sci. USA 74, 560–564 (1977)]. The DNA base sequence is compared with that of human interferon cDNA [Gene 10, 11–15 (1980)] whereby the obtained clone is confirmed to have a chromosomal gene corresponding to human interferon-$\beta$ messenger RNA, that is, human interferon-$\beta$ gene in chromosome.

The human interferon-$\beta$ gene and a DNA containing the gene and a DNA responsible for control of its transcription are recovered from the recombinant DNA obtained as above according to the method of Benton and Davis [Science, 196, 180–182 (1977)] or the method of Grunstein-Hogness [Proc. Natl. Acad. Sci. USA 72, 3961–3965 (1975)].

BRIEF DESCRIPTION OF THE DRAWINGS

FIG. 1-a shows a restriction endonuclease map of the 15 Kb chromosomal DNA fragment cloned in $\lambda$HIFN-$\beta_1$-121. Broken line in the figure indicates the arms of vector DNA derived from Charon 4A.

FIGS. 1-b and 1-d show a restriction endonuclease map of 1.8 Kb EcoRI fragment derived from human chromosomal DNA. Black box shows the region from which the messenger RNA is transcribed.

FIG. 1-c shows a region in human chromosomal DNA corresponding to interferon-$\beta$ cDNA. The open box in the figure indicates a protein coding region.

FIG. 1-e shows strategy for sequence determination. Arrows in the figure indicate the direction and extent of the sequence of each fragment analysed.

The following restriction endonucleases in FIG. 1 are described in the literature shown below.
Eco RI: Methods Mol. Biol. 7, 87 (1974)
Bgl II: Nucleic Acids Res., 3, 1747 (1976)
Hind III: J. Mol. Biol., 92, 331 (1975)
Bam HI: J. Mol. Biol., 97, 123 (1975)
Pst I: Nucleic Acids Res. 3, 343 (1976)
Pvu II: Gene 8, 329–343 (1980)
Hinf I: J. Mol. Biol., 110, 297 (1977)
Alu I: J. Mol. Biol., 102, 157 (1976)
Hae III: J. Virol., 10, 42 (1972)
Taq I: Proc. Natl. Acad. Sci. USA, 74, 542 (1977)
Ava II: Biochem. J., 159, 317 (1976)
Hin II: Gene 8, 329–343 (1980)
Eco RII: Nature New Biol., 244, 7 (1973)

FIG. 2 shows the base sequence of 1.8 Kb Eco RI fragment. The section numbered +1 to +561 indicates the sequence coding for the human interferon-$\beta$ protein, the arrows at −73 to −75 indicate the initiation site for transcription and the underline indicates the TATA box.

BEST MODE FOR CARRYING OUT THE INVENTION

The specific embodiment of the present invention is explained below.

EXAMPLE 1

Human gene library prepared by the following method was provided by Tom Maniatis (California Institute of Technology).

An entire chromosome DNA is extracted from human fetal liver with phenol, etc. and subjected to partial digestion with restriction endonucleases HaeIII and AluI.

About 18–25 Kb fragments in the obtained DNA fragments are concentrated according to sucrose density gradient centrifugation method. Then, the fragments are connected to the arm DNA of *Escherichia coli* phage$\lambda$ Charon 4A using a synthesized short chain nucleotide having a cleavage site for restriction endonuclease EcoRI to prepare an infectious phage recombinant DNA. Then, the recombinant is modified to a complete phage$\lambda$ particle according to packaging method for the purpose of enhancing the infectiousness. The resultant human gene library is in principle believed to be an assembly of recombinants containing 18–25 Kb human DNAs containing almost all human genes.

The recombinant phage having a DNA fragment containing human interferon-$\beta$ gene was selected from the human gene library using as a probe [$^{32}$P]-labelled cDNA fragment having the entire cDNA region translatable to human interferon-$\beta$ protein by the method of Benton and Davis [Science 196, 180–182 (1977)]. Details are illustrated below.

A DNA fragment of about 0.57 Kb having the cDNA region translatable to human interferon-$\beta$ protein and being used as a probe was prepared and radio-labelled as follows.

TpIF319-13 plasmid DNA is isolated from *Escherichia coli* $\chi$1776/TpIF319-13 ATCC 31712 having the recombinant plasmid TpIF319-13 containing the human interferon-$\beta$ cDNA by the method of Currier and Nester [Analyt. Biochem. 76, 431–441 (1976)] and digested with restriction endonucleases HincII, BglII and HhaI. The longest DNA fragment in the digest, i.e. 0.57 Kb DNA is the desired DNA fragment which is isolated by agarose electrophoresis according to the method of Tabak and Flavell [Nucleic Acids Research 5, 2321–2332 (1978)].

The DNA fragment is radio-labelled with [$^{32}$P] according to nick translation method [for example, Roop et al, Cell 15, 671–685 (1978)]. That is, 0.5 $\mu$g of the DNA was incubated at 15° C. in 30 $\mu$l of aqueous solution containing 50 mM Tris-HCl (pH 7.8), 5 mM MgCl$_2$, 10 mM $\beta$-mercaptoethanol, 5 $\mu$M dGTP, 150 $\mu$M dTTP, 1 ng of DNase I (product of Worthington), [$^{32}$P]-$\alpha$-dCTP (100 $\mu$Ci, 2000–300 Ci/mmol, product of RCC Amersham) and 15 units of DNA polymerase I (product of Boehringer Mannheim) for 4 hours. Then, EDTA is added to a final concentration of 20 mM and the mixture is incubated at 65° C. for 10 minutes to inactivate the enzyme. After removal of proteins with phenol, the mixture is subjected to Sephadex G-50 (product of Pharmacia Fine Chemicals) column chromatography for desalting. The thus obtained [$^{32}$P]-radio-labelled cDNA fragment to be used as a probe has about 10$^8$ cpm/$\mu$g radioactivity.

Using as a probe the DNA-fragment prepared by radio-labelling the human interferon-$\beta$ cDNA fragment, a recombinant phage having the DNA fragment containing human interferon gene is selected from the human gene library as follows.

The phage λ particles are dispersed on an agar plate [Science 202, 1279–1284 (1978)] to form phage plaques, the density of which is 10,000 to 30,000 per plate with a diameter of 15 cm.

A nitrocellulose paper (available from Schleicher and Schull) is put on the agar plate and marked for the definition of direction. The agar plate is allowed to stand at 4° C. for about 20 minutes to adsorb phages on the paper. The plate is kept at 4° C. and the nitrocellulose paper is air-dried at room temperature for about 90 minutes. It is soaked in an aqueous soltuion consisting of 0.1N NaOH and 1.5M NaCl for about 20 seconds to denature the phage DNAs. Then, they are neutralized in a solution of 0.2M Tris-HCl (pH 7.4) and 2×SSC (SSC means an aqueous solution consisting of 0.15M NaCl and 0.015M sodium citrate and 2×SSC means 2-fold concentrated SSC) for about 20 seconds and additionally in 2×SSC for about 20 seconds. After air-drying at room temperature for one hour and at 80° C. for 3 hours, the denatured phage DNAs are fixed on the nitrocellulose paper.

Hybridization of the phage DNAs on the nitrocellulose paper prepared above is carried out using the radio-labelled human interferon-β cDNA as a probe as follows.

The nitrocellulose paper is incubated in 3×SSC at 65° C. for 30 minutes and in a 3×SSC solution containing 0.2% polyvinylpyrrolidone (product of Nakarai Kagaku Co.), 0.2% bovine serum albumin (product of Iwai Kagaku Co.) and 0.2% Ficoll (product of Pharmacia Fine Chemicals) at 65° C. for 60 minutes. Then the paper is incubated at 65° C. in a hybridization solution consisting of 1M NaCl, 50 mM Tris-HCl (pH 8.0), 10 mM EDTA, 0.1% SDS, and 100 μg/ml ultrasonicated and heat-denatured *Escherichia coli* DNA for 60 minutes, whereby whole hybridization treatment is completed.

Separately, the radio-labelled probe DNA is denatured by heating at 95° C. for 10 minutes. Then, the pretreated nitrocellulose paper and the heat-denatured probe DNA are incubated in the hybridization solution mentioned above at 65° C. for hybridization. After 12 to 18 hours, the nitrocellulose paper is picked up, washed with 2×SSC twice, incubated at 65° C. in a solution containing 0.3×SSC and 0.1% SDS for 60 minutes twice, air-dried at 80° C. for one hour and subjected to radioautography using an X-ray film.

The radioautogram is put on the agar plate kept at 4° C. and the phages hybridized with the probe are scraped up. The procedure is repeated and recombinant phages having the DNA hybridized with human interferon-β cDNA are purified to monoclones.

Thus, 11 clones are obtained by screening about 100 million phage plaques.

The recombinant DNA of each clone is prepared by the method of Maniatis [Cell, 15, 687–701 (1978)] and used in the following analysis.

The recombinant DNA of each clone is cleaved with restriction endonuclease EcoRI and chain lengths of DNA fragments formed are determined by agarose gel electrophoresis. The DNA digests of all clones have 20 Kb and 11 Kb DNA fragments derived from the arms of vector phage λ Charon 4A as well as some DNA fragments derived from human chromosomal DNA. By the analysis, 11 clones are classified to 5 species. Further, the Southern hybridization [Southern, J. Mol. Biol. 98, 503–517 (1975)] is carried out using human interferon-β cDNA probe employed in the screening mentioned above to determine which DNA fragments obtained by the digestion with EcoRI hybridize with human interferon cDNA.

That is, the DNA in each phage clone is digested with EcoRI and subjected to agarose gel electrophoresis. Thereafter, gels are recovered by cutting and incubated at room temperature in an aqueous solution containing 0.5N NaOH and 1M NaCl to denature the DNA. The same procedure is repeated in an aqueous solution containing 0.5N Tris-HCl (pH 7.0) and 1.5M NaCl to neutralize the gel. The gel is put on a filter paper soaked with 20×SSC and a nitrocellulose paper is put on the gel. Then, a filter paper and a paper towel are put on the nitrocellulose paper to adsorb the denatured DNA in the gel thereon. After 12 to 18 hours, the nitrocellulose paper is peeled from the gel and air-dried at 80° C. for 3 hours to fix the DNA on the nitrocellulose paper. Hybridization is carried out in the same manner as in the screening of the phage mentioned above.

Thus it is confirmed that four species of the human chromosomal gene fragments in the five species have a 1.8 Kb DNA fragment formed by the treatment with EcoRI, referred to as EcoRI fragment hereinafter, and the 1.8 Kb EcoRI fragment has a structure complementary to human interferon cDNA. The other species is confirmed to have a DNA fragment containing a part of the 1.8 Kb EcoRI fragment.

Figure 1:
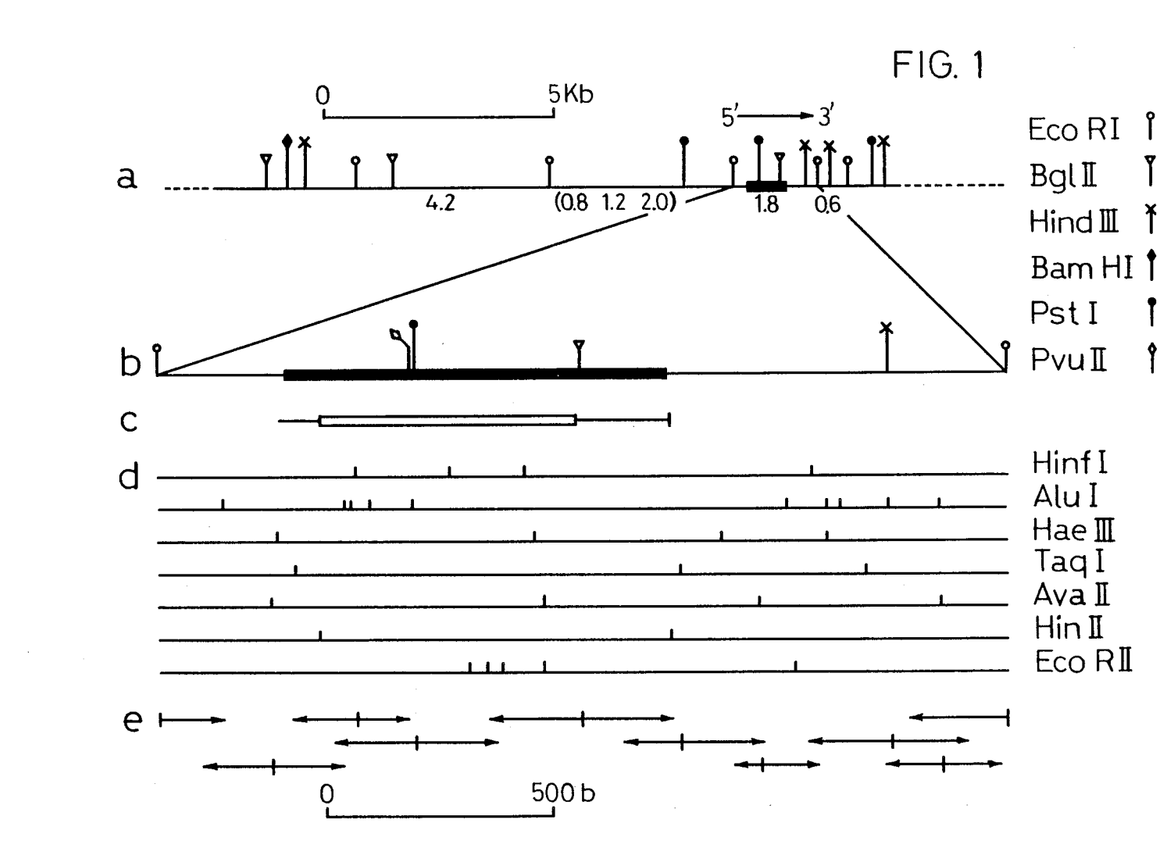

In the 11 clones, one of those which form 1.8 Kb EcoRI fragment is named λHIFN-$\beta_1$-121 and a cleavage map for restriction endonucleases is prepared based on the experiments using restriction endonucleases such as HindIII, BamHI, BglII, PstI and the like. The map is illustrated in FIG. 1-$a$.

In order to investigate the 1.8 Kb EcoRI fragment showing complementarity to the human interferon-β cDNA, the fragment is recloned using plasmid pBR322 as a vector as follows.

1 μg of λHIFN-$\beta_1$-121 DNA is digested with restriction endonuclease EcoRI and the cohesive ends with EcoRI are rendered flush with 5 units of DNA polymerase Klenow fragment (product of Boehringer Mannheim) in 30 μl of an aqueous solution containing 0.1M potassium phosphate buffer solution (pH 6.9), 6 mM $MgCl_2$, 6 mM mercaptoethanol, 1 mM ATP and 1 mM TTP. After removal of proteins with phenol, the residue is treated at 37° C. with 30 μl of a reaction solution consisting of 1 μg of DNA, 0.14M potassium cacodilate (pH 7.6), 0.03M Tris, 0.1 mM dithiothreitol, 1 mM $CaCl_2$, 1 mM dCTP and 2 units of terminal transferase for 15 minutes to tail the 3' ends of the EcoRI fragment with about 100 deoxycytidine residues. Separately, a vector is prepared by cutting pBR322 with PstI and tailing the 3' ends of the PstI fragment with about 100 deoxyguanine residues. 0.05 μg of the thus obtained EcoRI fragment of human chromosomal gene DNA and 0.05 μg of pBR322 DNA are incubated at 65° C. for 2 hours, at 45° C. for one hour, at 37° C. for one hour and at room temperature for one hour in a solution consisting of 0.1M NaCl, 50 mM Tris-HCl (pH 7.5), and 5 mM EDTA to hybridize them. *Escherichia coli* χ1776 is subjected to transformation with the reaction mixture by the method of Enea et al. [J. Mol. Biol. 96, 495–509 (1975)]. Tetracycline resistant strains are picked up and the DNA of 400 strains are fixed on a nitrocellulose paper [Grunstein-Hogness method, Proc. Natl. Acad. Sci. USA 72, 3961–3965 (1975)]. Hybridization is carried out on the nitrocellulose paper in the same manner as in the above screening of phages and Southern hybridization wherein a DNA is fragmented by heating in alkali in a hybridization solution and heat-denatured pBR322 DNA is added in a concentration of 30 μg/ml, using the same probe of human interferon -β cDNA to select the *Escherichia coli* strains having a recombinant plasmid containing 1.8 Kb EcoRI fragment.

A recombinant plasmid DNA having 1.8 Kb EcoRI fragment containing a recombinant DNA hybridizing with human interferon-β cDNA is prepared from the thus obtained *Escherichia coli* strain by the method of Currier and Nester mentioned above and analysed as follows.

It is apparent from the above that 1.8 Kb EcoRI fragment derived from the human chromosomal DNA contains a DNA complementary to the messenger RNA of human interferon-β DNA. For further clarification, a cleavage map for restriction endonucleases is prepared by measuring by agarose electrophoresis, etc. the chain lengths of the DNA fragments formed by cutting the recombinant plasmid DNA or a part thereof with one or more restriction endonucleases or by partially digesting the fragment labelled with [$^{32}$P] at the 3′ ends using polynucleokinase [Smith and Birnstiel, Nucleic Acids Res., 3, 2387–2398 (1976)] (FIG. 1-*b*, 1-*d*). FIG. 1-*c* shows the region corresponding to interferon-β cDNA wherein the open box indicates the protein coding region. The same region as the cDNA is found in the cleavage map. It is apparent from the foregoing that 1.8 Kb EcoRI DNA fragment derived from human chromosomal DNA has the same sequence as that of human interferon-β messenger RNA, i.e. cDNA and that 1.8 Kb EcoRI DNA fragment contains human interferon-β gene in chromosome (the black box in FIG. 1-*b*).

It has been revealed that intervening sequences, introns, present in the gene of many eucaryotic cells are absent in the human interferon-β gene. The absence of intervening sequences in the interferon-β gene in 1.8 Kb EcoRI fragment suggests that the gene DNA is applicable to the production of interferon proteins by procaryotic organisms not having the mechanism removing the intervening sequence such as *Escherichia coli*.

In order to prove the foregoing, the base sequence of the 1.8 Kb EcoRI fragment is determined by the method of Maxam and Gilbert [Proc. Natl. Acad. Sci. USA 74, 560–564 (1977)]. The result is shown in FIG. 2. The 1.8 Kb EcoRI fragment introduced into *Escherichia coli* has been deposited with the American Type Culture Collection in U.S.A. as *Escherichia coli* CI4 under accession number ATCC 31905.

We claim:

1. A DNA consisting essentially of a DNA containing a human interferon β gene and a human interferon-β gene control DNA responsible for controlling the transcription of said human interferon-β gene which has a nucleotide sequence, as follows:

TA TAA ATA GGC CAT ACC CAC GGA GAA AGG
   |
  −100

<u>ACA TTC TAA CTG CAA CCT TTC GAA GCC TTT GCT</u>
                                        |
                                       −50

CTG GCA CAA CAG GTA GTA GGC GAC ACT GTT CGT

GTT GTC AAC ATG ACC AAC AAG TGT CTC CTC CAA
        |   |
       −1  +2

ATT GCT CTC CTG TTG TGC TTC TCC ACT ACA GCT
                                     |
                                    50

CTT TCC ATG AGC TAC AAC TTG CTT GGA TTC CTA

CAA AGA AGC AGC AAT TTT CAG TGT CAG AAG
                |
               100

CTC CTG TGG CAA TTG AAT GGG AGG CTT GAA
                                     |
                                    150

TAC TGC CTC AAG GAC AGG ATG AAC TTT GAC ATC

CCT GAG GAG ATT AAG CAG CTG CAG CAG TTC
                        |
                       200

CAG AAG GAG GAC GCC GCA TTG ACC ATC TAT

GAG ATG CTC CAG AAC ATC TTT GCT ATT TTC
        |
       250

AGA CAA GAT TCA TCT AGC ACT GGC TGG AAT
                                     |
                                    300

GAG ACT ATT GTT GAG AAC CTC CTG GCT AAT

GTC TAT CAT CAG ATA AAC CAT CTG AAG ACA
                                 |
                                350

GTC CTG GAA GAA AAA CTG GAG AAA GAA GAT

TTC ACC AGG GGA AAA CTC ATG AGC AGT CTG
        |
       400

CAC CTG AAA AGA TAT TAT GGG AGG ATT CTG
                                     |
                                    450

CAT TAC CTG AGG GCC AAG GAG TAC AGT CAC TGT

GCC TGG ACC ATA GTC AGA GTG AAA ATC CTA
                    |
                   500

AGG AAC TTT TAC TTC ATT AAC AGA CTT ACA

GGT TAC CTC CGA AAC
                            |
                           550

2. A recombinant DNA comprising a vector DNA having a foreign DNA containing a human interferon-β gene and a human interferon β gene control DNA responsible for controlling the transcription of said human interferon-β gene which has a nucleotide sequence, as follows:

TA TAA ATA GGC CAT ACC CAC GGA GAA AGG
   |
  −100

<u>ACA TTC TAA CTG CAA CCT TTC GAA GCC TTT GCT</u>
                                        |
                                       −50

CTG GCA CAA CAG GTA GTA GGC GAC ACT GTT CGT

GTT GTC AAC ATG ACC AAC AAG TGT CTC CTC CAA
        |   |
       −1  +2

ATT GCT CTC CTG TTG TGC TTC TCC ACT ACA GCT
                                     |
                                    50

-continued

CTT TCC ATG AGC TAC AAC TTG CTT GGA TTC CTA

CAA AGA AGC AGC AAT TTT CAG TGT CAG AAG
                              |
                             100

CTC CTG TGG CAA TTG AAT GGG AGG CTT GAA
                                      |
                                     150

TAC TGC CTC AAG GAC AGG ATG AAC TTT GAC ATC

CCT GAG GAG ATT AAG CAG CTG CAG CAG TTC
                       |
                      200

CAG AAG GAG GAC GCC GCA TTG ACC ATC TAT

GAG ATG CTC CAG AAC ATC TTT GCT ATT TTC
             |
            250

AGA CAA GAT TCA TCT AGC ACT GGC TGG AAT
                                      |
                                     300

-continued

GAG ACT ATT GTT GAG AAC CTC CTG GCT AAT

GTC TAT CAT CAG ATA AAC CAT CTG AAG ACA
                              |
                             350

GTC CTG GAA GAA AAA CTG GAG AAA GAA GAT

TTC ACC AGG GGA AAA CTC ATG AGC AGT CTG
                  |
                 400

CAC CTG AAA AGA TAT TAT GGG AGG ATT CTG
                                      |
                                     450

CAT TAC CTG AGG GCC AAG GAG TAC AGT CAC TGT

GCC TGG ACC ATA GTC AGA GTG AAA ATC CTA
                      |
                     500

AGG AAC TTT TAC TTC ATT AAC AGA CTT ACA

GGT TAC CTC CGA AAC
         |
        550 inserted therewith.

* * * * *

UNITED STATES PATENT AND TRADEMARK OFFICE
CERTIFICATE OF CORRECTION

PATENT NO. : 4,738,931

DATED : April 19, 1988

INVENTOR(S) : HARUO SUGANO, ET AL.

Page 1 of 5

It is certified that error appears in the above-identified patent and that said Letters Patent is hereby corrected as shown below:

IN THE DRAWINGS:

After Fig. 1, add the following Figures 2-1, 2-2 and 2-3

```
                                        -- GAATTCTCAGGTCGTTTGCTTTCCTTTGCTTTCTCCCAAGTCTTGTTTTACAATTTG
                                                            -350
CTTTAGTCATTCACTGAAACTTTAAAAAACATTAGAAAACCTCACAGTTTGTAAATCTTTTTCCCTATTATATATATCATAAGATAGGATCTTAAATAAA
-300                                    -250
GAGTTTTAGAAACTACTAAAATGTAAATGACATAGGAAAACTGAAAGGGAGAAGTGAAAGTGGGAAATTCCTCTGAATAGAGAGAGGACCATCTCATATA
-200                                    -150
AATAGGCCATACCCACGGAGAAAGGACATTCTAACTGCAACCTTTCGAAGCCTTTGCTCTGGCACAACAGGTAGTAGGCGACACTGTTCGTGTTGTCAAC
-100                                    -50                                                     -1 met thr asn lys cys leu leu gln ile ala leu leu leu cys phe ser thr thr ala leu ser MET SER TYR ASN
ATG ACC AAC AAG TGT CTC CTC CAA ATT GCT CTC CTG TTG TGC TTC TCC ACT ACA GCT CTT TCC ATG AGC TAC AAC
+1                                                              50

LEU LEU GLY PHE LEU GLN ARG SER SER ASN PHE GLN CYS GLN LYS LEU LEU TRP GLN LEU ASN GLY ARG LEU GLU
TTG CTT GGA TTC CTA CAA AGA AGC AGC AAT TTT CAG TGT CAG AAG CTC CTG TGG CAA TTG AAT GGG AGG CTT GAA
                      100                                                                       150

TYR CYS LEU LYS ASP ARG MET ASN PHE ASP ILE PRO GLU GLU ILE LYS GLN LEU GLN GLN PHE GLN LYS GLU ASP
TAC TGC CTC AAG GAC AGG ATG AAC TTT GAC ATC CCT GAG GAG ATT AAG CAG CTG CAG CAG TTC CAG AAG GAG GAC
                                                            200
```

FIG. 2-1

UNITED STATES PATENT AND TRADEMARK OFFICE
CERTIFICATE OF CORRECTION

PATENT NO. : 4,738,931

DATED : April 19, 1988

INVENTOR(S) : HARUO SUGANO, ET AL.

Page 2 of 5

It is certified that error appears in the above-identified patent and that said Letters Patent is hereby corrected as shown below:

```
ALA ALA LEU THR ILE TYR GLU MET LEU GLN ASN ILE PHE ALA ILE PHE ARG GLN ASP SER SER SER THR GLY TRP
GCC GCA TTG ACC ATC TAT GAG ATC CTC CAG AAC ATC TTT GCT ATT TTC AGA CAA GAT TCA TCT AGC ACT GGC TGG
                        250                                                                      300

ASN GLU THR ILE VAL GLU ASN LEU LEU ALA ASN VAL TYR HIS GLN ILE ASN HIS LEU LYS THR VAL LEU GLU GLU
AAT GAG ACT ATT GTT GAG AAC CTC CTG GCT AAT GTC TAT CAT CAG ATA AAC CAT CTG AAG ACA GTC CTG GAA GAA
                                                            350

LYS LEU GLU LYS GLU ASP PHE THR ARG GLY LYS LEU MET SER SER LEU HIS LEU LYS ARG TYR TYR GLY ARG ILE
AAA CTG GAG AAA GAA GAT TTC ACC AGG GGA AAA CTC ATG AGC AGT CTG CAC CTG AAA AGA TAT TAT GGG AGG ATT
                        400                                                                      450

LEU HIS TYR LEU LYS ALA LYS GLU TYR SER HIS CYS ALA TRP THR ILE VAL ARG VAL GLU ILE LEU ARG ASN PHE
CTG CAT TAC CTG AGG GCC AAG GAG TAC AGT CAC TGT GCC TGG ACC ATA GTC AGA GTG GAA ATC CTA AGG AAC TTT
                                                            500

TYR PHE ILE ASN ARG LEU THR GLY TYR LEU ARG ASN
TAC TTC ATT AAC AGA CTT ACA GGT TAC CTC CGA AAC TGA AGATCTCCTAGCCTGTGCCTCTGGGACTGGACAATTGCTTCAAGCATT
                        550                                                                     600
```

FIG.2-2

UNITED STATES PATENT AND TRADEMARK OFFICE
CERTIFICATE OF CORRECTION

PATENT NO. : 4,738,931
DATED : April 19, 1988
INVENTOR(S) : HARUO SUGANO, ET AL.

Page 3 of 5

It is certified that error appears in the above-identified patent and that said Letters Patent is hereby corrected as shown below:

```
CTTCAACCAGCAGATGCTGTTTAAGTCACTGATGGCTAATGTACTGCATATGAAAGGACACTAGAAGATTTTGAAATTTTTATTAAATTATGAGTTATTT
                                        650                                                     700
TTATTTATTTAAATTTTATTTTGGAAAATAAATTATTTTTGGTGCAAAAGTCAACATGGCAGTTTTAATTTGGATTTGATTTATATAACCATCCATATTA
                     750                                                                        800
TAAAATTGCCAAGTACCTATTAGTTGTTCTTTTTAAAATATACCTGCAAAGTAGTATACTTTCTGGCCCCTGCCTTTAAGGAATTTAAAATTCAAGAAAG
                         850                                                                   900
CCATGATGGAATATATAAGGTAAGAGACAATAAGGGGACCTGAACCTTATGGGGGAATAAATATGGCATGAACTGCTGTGGGATTAAAAGAGAAAAGGAA
                        950                                                                   1000
AGCTGGAGGGTCTGCAACTAAACCTGGGGTTCCCATTCCTCCTACTGTGTGTTCCAGATTCTCTCATCATAAAGTTAGAATTGAGCTGGCCATCAGGAAT
                       1050                                                                   1100
AGCCAGAGGAATATGTCAGCTTTTGTGTTCTCCCTAACCTTCCCCAGTTATTTGGGGGATCACTTTGCTCCTCGAAAGATTTTTAAATAATTATGTGCCC
                       1150                                                                   1200
CCCACCATCCCTGCAAGCTTAAGGGTGAGAAGTCCCATTTACTTCCATGACACTATTAAGCAGCAATCTCTTTATTCTGCTCATCATGGGACAGCCAAGA
                       1250                                                                   1300
TGTGTGGGTATCTTAGGGGACCTGTGGGTCCCTGTCTCCTGGCATGGCACAGGCATCAGAGGAAGAAGAACCTTTTTATACCCTAGCCATCTGGTTACTT
                       1350                                                                   1400
TTCTCCCTAGTTTTTCAAAAAACTAAGCCTGCTTCCAGTCCCCACTGCCTTGTTCATACAGAATTC
                       1450
```

FIG.2-3 --.

UNITED STATES PATENT AND TRADEMARK OFFICE
CERTIFICATE OF CORRECTION

PATENT NO. : 4,738,931
DATED : April 19, 1988          Page 4 of 5
INVENTOR(S) : HARUO SUGANO, ET AL.

It is certified that error appears in the above-identified patent and that said Letters Patent is hereby corrected as shown below:

Cover Page, at [57] IN THE ABSTRACT:

"2 Claims, 1 Drawing Sheet" should read:

--2 Claims, 4 Drawing Sheets--.

Column 7, line 62,

"ACA TTC TAA CTG CAA CCT TTC GAA GCC TTT GCT"
$-50$ should read:

--ACA TTC TAA CTG CAA CCT TTC GAA GCC TTT GCT--.
$-50$

UNITED STATES PATENT AND TRADEMARK OFFICE
CERTIFICATE OF CORRECTION

PATENT NO. : 4,738,931

DATED : April 19, 1988

INVENTOR(S) : HARUO SUGANO, ET AL.

Page 5 of 5

It is certified that error appears in the above-identified patent and that said Letters Patent is hereby corrected as shown below:

Column 8, line 59,

" ACA TTC TAA CTG CAA CCT TTC GAA GCC TTT GCT "
$$-50$$

should read:

-- ACA TTC TAA CTG CAA CCT TTC GAA GCC TTT GCT --.
$$-50$$

Signed and Sealed this

Twenty-third Day of August, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,738,931
DATED : April 19, 1988
INVENTOR(S) : HARUO SUGANO, ET AL

It is certified that error appears in the above-identified patent and that said Letters Patent is hereby corrected as shown below:

On the title page under Related U.S. Application Data after "Sep. 30, 1982, abandoned insert --filed as PCT JP82/00034 on Feb. 4, 1982, published as WO82/02715 on Aug. 19, 1982, now abandoned--.

Signed and Sealed this

Fifteenth Day of November, 1988

Attest:

DONALD J. QUIGG

Attesting Officer     Commissioner of Patents and Trademarks